US012741950B1

(12) United States Patent
Harvey et al.

(10) Patent No.: US 12,741,950 B1
(45) Date of Patent: Sep. 22, 2026

(54) COUMARIN-BASED THERMOSETS AND THERMOPLASTICS

(71) Applicant: The United States of America, as represented by the Secretary of the Navy, Arlington, VA (US)

(72) Inventors: Benjamin G. Harvey, Ridgecrest, CA (US); Joshua E. Baca, Ridgecrest, CA (US); Michael D. Garrison, Ridgecrest, CA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 408 days.

(21) Appl. No.: 18/479,998

(22) Filed: Oct. 3, 2023

(51) Int. Cl.
*C07D 311/74* (2006.01)
*C07D 311/80* (2006.01)
*C08G 59/26* (2006.01)

(52) U.S. Cl.
CPC .......... *C07D 311/74* (2013.01); *C07D 311/80* (2013.01); *C08G 59/26* (2013.01)

(58) Field of Classification Search
CPC ...... C07D 311/74; C07D 311/80; C08G 59/26
See application file for complete search history.

(56) References Cited

FOREIGN PATENT DOCUMENTS

| | | | | | | |
|---|---|---|---|---|---|---|
| CA | 2905995 | A1 | * | 9/2014 | ........... | C07C 237/20 |
| CN | 113249281 | A | * | 8/2021 | ........... | C12N 9/0006 |
| CN | 116217423 | A | * | 6/2023 | ........... | C07C 231/02 |
| RU | 2799566 | C1 | * | 7/2023 | | |

* cited by examiner

*Primary Examiner* — Rabon A Sergent
(74) *Attorney, Agent, or Firm* — Naval Air Warfare Center Weapons Division; Edu Enin-Okut

(57) ABSTRACT

The invention relates to a method of synthesizing less toxic, sustainable bisphenols having a coumarin-type structure and the polymers derived therefrom. The method synthesizes the bisphenolic coumarins from biologically derived phlorogincol and β-keto esters. The bisphenolic coumarins can be converted coumarin-based polymers including engineering thermoplastics and high-performance thermosetting resins.

11 Claims, 6 Drawing Sheets

COUMARIN-BASED THERMOSETS AND THERMOPLASTICS

STATEMENT REGARDING FEDERALLY SPONSORED RESEARCH OR DEVELOPMENT

The invention described herein may be manufactured and used by or for the government of the United States of America for governmental purposes without the payment of any royalties.

FIELD OF INVENTION

This invention is related to methods to produce bisphenolic coumarins from biologically-based compounds, and coumarin-based polymers produced therefrom.

BACKGROUND

A wide variety of conventional thermosetting and thermoplastic polymers are derived from bisphenols, primarily bisphenol A (BPA). Epoxy-amine thermosetting resins are ubiquitous and heavily used in the composites, adhesives, and electronics industries. The diglycidyl ether of bisphenol A (DGEBA) is the predominant epoxy in nearly all commercial applications, but concerns about BPA use have risen in several countries because the chemical is estrogenic, which can negatively impact public health. In addition, the phenols used to produce bisphenol are mostly obtained from unsustainable, petrochemical sources.

SUMMARY

The method described herein produce less toxic, sustainable bisphenols having a coumarin-type structure that can be used as precursors to engineering thermoplastics and high-performance thermosetting resins. The bisphenolic coumarins produced by the method use biologically derived phloroglucinol and β-keto esters. The properties of the resulting polymers can be easily modified and optimized through careful selection of the β-keto ester and modification of the bisphenolic coumarin structure (e.g., via hydrogenation and/or the addition of functional groups). These polymers have applications in, for example, coatings, adhesives, structural materials, fabrics, and aerospace composites.

DETAILED DESCRIPTION

The method described below produces a new class of monomers based on a coumarin scaffold and polymers produced therefrom. These materials can be readily synthesized from sustainable reagents, and their material properties can be controlled through substitution of the coumarin ring system. An example of the method is illustrated in FIG. 1.

Figure 1:
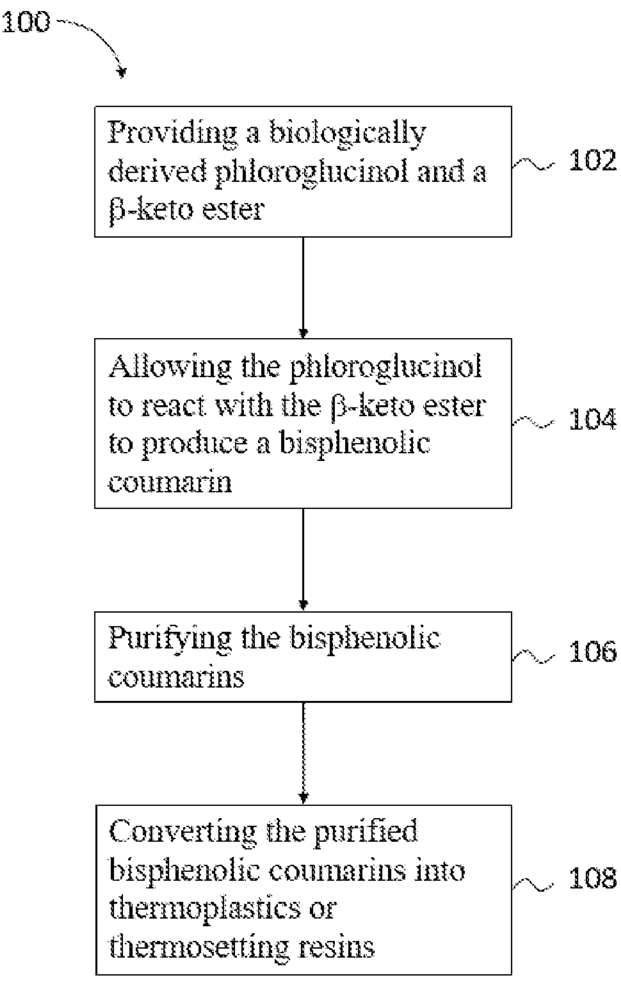
FIG. 1 is a flow diagram depicting an example of the method for synthesizing bisphenolic coumarins from biologically derived phloroglucinol and β-keto esters.

In FIG. 1, the method 100 for producing a coumarin-based thermosets and thermoplastics begins at step 102 by providing a phloroglucinol derived from biological source materials and a β-keto ester or mixtures thereof. Next, at step 104, the phloroglucinol is allowed to react with the β-keto ester in the presence of an acid catalyst at elevated temperatures which produces a bisphenolic coumarin. The bisphenolic coumarin is purified at step 106. Then, at step 108, the purified bisphenolic coumarin is converted into a thermoplastic or a thermosetting resin.

As noted in the example of the method discussed above, the preferred phloroglucinol used is biologically derived. For example, the phloroglucinol can be produced via fermentation or easily generated from other biologically based compounds such as naringenin.

β-keto esters having functional groups that remain stable under the reaction conditions of the method can be used. Examples of β-keto esters suitable for use in the method include ethyl acetoacetate, ethyl-2-oxocyclohexane carboxylate, ethyl benzoylacetate, and ethyl-4,4,4-trifluoroacetoacetate. Further, and similar to phloroglucinol, the β-keto esters can also be produced from sustainable materials. For example, ethyl acetoacetate can be prepared from biologically-based ethyl acetate.

Synthesis of the bisphenolic coumarins using phloroglucinol and β-keto esters is accomplished via a Pechman reaction. Catalysts used in the reaction can be acid catalysts. Suitable acid catalysts include Lewis acid catalysts, such as zirconium tetrachloride. The temperature of the reaction ranges from about 50° C. to about 150° C. Below about 50° C., the reaction proceeds at a much slower rate which is undesirable for manufacturing the bisphenolic coumarins at levels high enough for practical applications and industrial production. Above about 150° C., there is a much higher probability of the development of side reactions and/or the degradation of the product. Preferably, the reaction is performed at 100° C. to synthesize bisphenolic coumarins at a desirable rate while avoiding side reactions and product degradation. The preferred reaction time ranges from about 5 minutes to about 30 minutes.

The synthesis of the bisphenolic coumarins via the Pechman reaction can be conducted without the addition of solvent. An example of the Pechman reaction, and the bisphenolic coumarins that can synthesized, is depicted in Scheme I below.

Scheme I

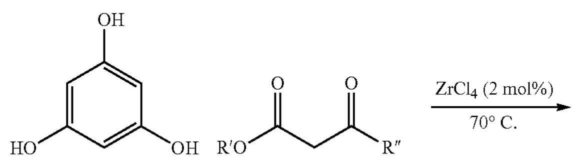

-continued

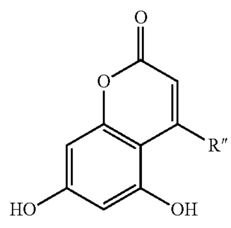

In Scheme I, preferably R' represents a short chain alkyl group (such as an ethyl group) and R" represents an alkyl group, an aryl group, a halogenated alkyl group, a halogenated aryl group, and/or an alkene-containing group. It is preferred that the bisphenolic coumarins produced by Scheme I are substituted. More preferably, the substituted bisphenolic coumarins produced include 5,7-dihydroxy-4-methyl-2H-chromen-2-one (Me-CMRN), 4-ethyl-5,7-dihydroxy-2H-chromen-2-one (Et-CMRN), 1,3-dihydroxy-7,8,9,10-tetrahydro-6H-benzo[c]chromen-6-one (C6-CMRN), and 5,7-dihydroxy-4-phenyl-2H-chromen-2-one (Ph-CMRN). The Pechman reaction depicted in Scheme I can produce substituted bisphenolic coumarins in yields of up to about 74%.

The bisphenolic coumarins can be purified by recrystallization and washing with a non-polar solvent to remove, for example, residual staring materials, side products, and catalyst residue. Examples of solvents that can used when recrystallizing the bisphenolic coumarins include ethanol, methanol, isopropanol, tetrahydrofuan (THF), and dimethyl ether (DME). Alternatively, the bisphenolic coumarins can be purified by column chromatography.

Purified bisphenolic coumarins can be converted into thermoplastics and thermosetting resins. Examples of thermoplastics that can be generated from the bisphenolic coumarins include polycarbonates, polyesters, and polysulfones. The polycarbonates can be synthesized from the reaction of the bisphenolic coumarins with phosgene or diphenylcarbonate. Polyesters can be synthesized from the bisphenolic coumarins and diacids in the presence of a base. Polysulfones can be synthesized from the bisphenolic coumarins by reaction with reagents such as bis(4-chlorophenyl) sulfone.

Thermosetting resins that can be produced from the purified bisphenolic coumarins include epoxies, cyanate esters, propargyl ethers, and phthalonitriles through reaction with epichlorohydrin, cyanogen halides, propargyl halides, and 4-nitrophthalonitrile, respectively. For example, epoxies can be generated when purified, substituted bisphenolic coumarins are epoxidized via a substitution reaction with (±)-epichlorohydrin, a base, and an alcoholic solvent at 90° C. as depicted in Scheme II below. Preferably, the base used in the epoxidation reaction is sodium hydroxide (NaOH) or potassium hydroxide (KOH). Alcoholic solvents suitable for use in the reaction include ethanol (EtOH) and isopropyl alcohol. The epoxidation reaction depicted in Scheme II can produce courmarin-based epoxy monomers in yields of up to about 83%.

Scheme II

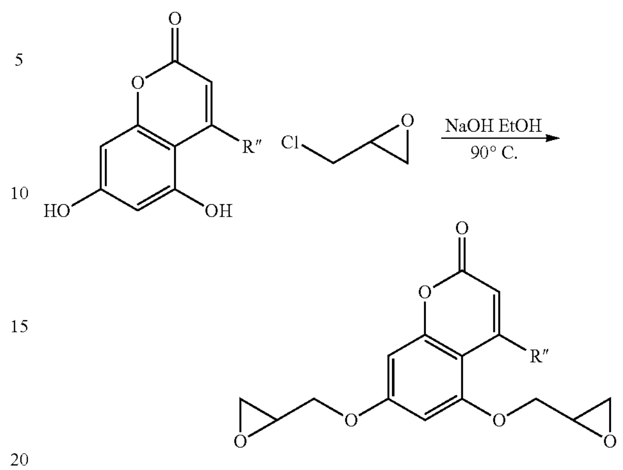

Examples of coumarin-based epoxy monomers generated via the epoxidation reaction in Scheme II-4-methyl-5,7-bis(oxiran-2-ylmethoxy)-2H-chromen-2-one (Me-CMRN-EP), 4-ethyl-5,7-bis(oxiran-2-ylmethoxy)-2H-chromen-2-one (Et-CMRN-EP), 1,3-bis(oxiran-2-ylmethoxy)-7,8,9,10-tetrahydro-6H-benzo[c]chromen-6-one (C6-CMRN-EP), and 5,7-bis(oxiran-2-ylmethoxy)-4-phenyl-2H-chromen-2-one (Ph-CMRN-EP)—are depicted below. To create polymer networks from the epoxy monomers, the monomers can be cured with a curing agent such as 4,4'-methylenebis-2-ethyl-6-methylaniline (MeEtMDA). Preferably, a protocol of curing the coumarin-based epoxy monomers at 180° C. for 8 hours is used to form the coumarin-based polymer networks.

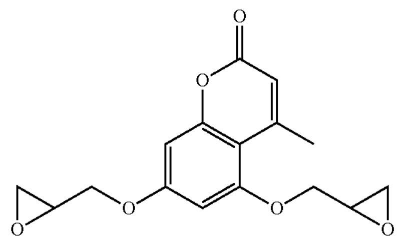

Me-CMRN-EP

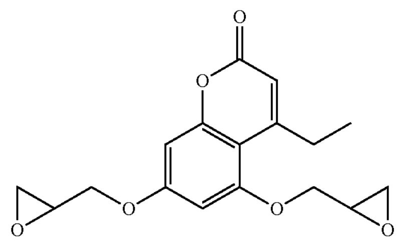

Et-CMRN-EP

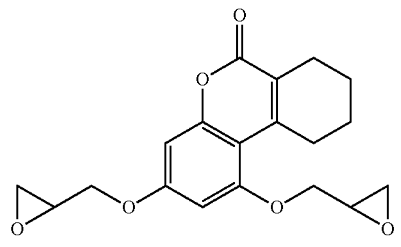

C6-CMRN-EP

-continued

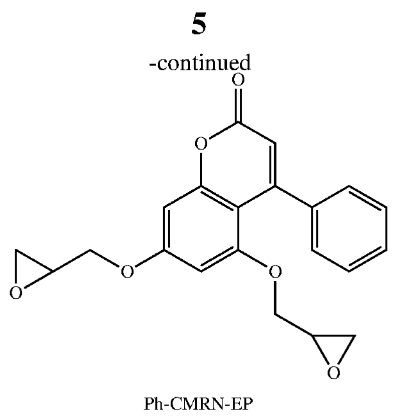

Ph-CMRN-EP

In addition, the bisphenolic coumarins can be converted to vinyl esters through esterification of a coumarin-based bisepoxide. Benzocyclobutenes can be obtained by reaction of the bisphenolic coumarins with 4-bromobenzocyclobutene in the presence of a base. Cross-linking of coumarin-based thermosetting resins can be accomplished through the application of heat either with or without catalysts.

Coumarin-based polymers produced using the method described herein, such as the coumarin-based thermosetting resins, can be combined with a structural support including carbon fiber, glass fiber, quartz fiber, Si—C fabric, carbon nanotubes, carbon nanotube sheets, boron nitride fibers, boron nitride nanotubes and other boron nitride nanomaterials. Then, the combination can be cured to obtain composite structures. The coumarin-based polymers have physical characteristics (e.g., activation energy ($E_a$), decomposition temperatures, char yields) and processing parameters comparable to the range expected for traditional thermosets and thermoplastics. Thus, these polymers can be employed without any modification to widely-used manufacturing equipment to make products without any concerns about product performance. The ability to use biologically-based source materials for the production of polymers will allow for on-demand domestic production of a wide variety of materials while reducing supply chain logistics.

EXAMPLES

The following examples are given as particular embodiments of the invention and to demonstrate the practice and advantages thereof. It is to be understood that the examples are given by way of illustration and are not intended to limit the specification or the claims that follow in any manner.

Methods of Characterization

Nuclear Magnetic Resonance (NMR) Spectroscopy. $^{1}H$ and $^{13}C$ NMR spectra were collected on a Bruker AVANCE II 500 MHz spectrometer. The NMR samples were analyzed in DMSO-$d^6$ using the solvent peaks as references [DMSO-$d^6$: δ 2.54 ($^{1}H$), 40.45 ($^{13}C$)].

Differential Scanning calorimetry (DSC). DSC was performed on the epoxy resins to determine the melting point ($T_m$) and on the epoxy-amine mixtures to determine the cure chemistry. The DSC studies were performed on a TA Instruments Q200 differential scanning calorimeter calibrated with indium. The samples were from about 2 mg to about 5 mg and contained in hermetically sealed aluminum pans. The epoxy resins were analyzed from −50° C. to 200° C., and the epoxy-amine blends were analyzed from −50° C. to 300° C. The heating rate for the epoxy resins was 10° C./minute, and was 2, 4, 6, 8, and 10° C./minute for the epoxy-amine mixtures. The experiments were performed under a nitrogen atmosphere, which had a flow rate of 50 mL/minute.

Thermogravimetric Analysis (TGA). TGA experiments were performed on a TA Instruments Q5000 thermogravimetric analyzer under nitrogen or air atmosphere. The flow rate of the carrier gas was 25 mL/minute, and the samples were analyzed from 50° C. to 600° C. at a heating rate of 10° C./minute. The decomposition temperature ($T_d$) was reported as the temperature at which 5% mass loss has occurred. The $T_d$ and char yield are reported as an average of three runs in each atmosphere (nitrogen or air).

Dynamic-Mode Thermomechanical Analysis (TMA). Dynamic-mode TMA experiments were performed on samples using a TA Instruments 450EM thermomechanical analyzer in a three-point bending mode. Samples were about 20 mm×3 mm×2 mm in size. A preload force of 0.20 N was applied to the sample prior to starting the run, and scans were performed with a frequency of 0.10 hertz with a force amplitude of 0.08 N. The experiments were performed from −50° C. to 250° C. with chiller attachment.

Ultra Violet-Visible (UV-VIS) Spectroscopy. Ultraviolet-visible (UV-VIS) absorbance spectroscopy was performed using a CRAIC Technologies UV-visible-NIR Microspectrometer with a 40× objective and 1-micron spot size. The microspectrometer was calibrated with NIST alumina and silver standards. The UV-VIS measurements were performed on circular resin plaques.

Fourier Transform Infrared (FTIR) Spectroscopy. FTIR was performed on a Thermo Fisher Nicolet 6700 fourier transform infrared spectrometer with attenuated total reflectance (ATR) smart iTR accessory. The detector was a liquid nitrogen cooled MCTA detector. A germanium window was used for the FTIR-ATR experiments. Each FTIR experiment consisted of 32 scans with a resolution of 4 $cm^{-1}$. Baseline subtraction (clean germanium window) and corrections were performed.

Nonisothermal Kinetics Analysis. The cure kinetics were analyzed using multiple heating rate kinetics via DSC then applying the Kissinger and Flynn-Wall-Ozawa models to determine the activation energy ($E_a$) and collision factor (A). The uncured reaction mixtures were analyzed at heating rates of 10, 8, 6, 4, and 2° C./minute. For the Kissinger model, the peak exotherm temperature is determined from the peak exotherm temperature ($T_p$) using the following equation (1):

$$\ln\left(\frac{\beta}{T_p^2}\right) = \ln\left(\frac{AR}{E_a}\right) - \frac{E_a}{RT_p} \quad (1)$$

where β is the heating rate and R is the ideal gas constant. For each heating rate, $\ln(\beta/T_p^2)$ was plotted versus $1/T_p$ then $E_a$ and A were determined from the slope and y-intercept of the resulting line. To determine the values of $E_a$ at various degrees of cure (α), the Flynn-Wall-Ozawa model was applied at α values from 0.05 to 0.95 in increments of 0.05. The Flynn-Wall-Ozawa model, equation (2), is as follows:

$$\log(\beta) = \log\left(\frac{AE_a}{R*g(\alpha)}\right) - 2.315 - \frac{0.4567E_a}{RT} \quad (2)$$

In the Flynn-Wall-Ozawa model, g(α) is the α-dependent conversion function and depends on reaction type (i.e.

unimolecular, bimolecular, autocatalytic). Thus, by plotting log(β) versus 1/T for a given value of α, the value of $E_a$ can be determined from the slope of the line. Because this value can be determined regardless of reaction model (g(α)), the Flynn-Wall-Ozawa model is considered a "reaction-free" model.

Isothermal Kinetics Analysis. To determine optimal curing temperatures and times, isothermal kinetics studies were performed on the uncured epoxy-amine solutions at 150° C. and 180° C. The uncured epoxy-amine solutions were added in amounts of about 2 mg to about 5 mg to aluminum hermetic pans. Then, the pans were placed in an oven under nitrogen at the desired temperature. For each temperature, the samples were analyzed by DSC after curing for various times up to 48 hours.

Density Measurements. Cured network density was determined on a Micrometrics Accupyc 1330 pycnometer using helium gas. A 0.7167 $cm^3$ ball bearing standard was used to calibrate the pycnometer. Sample sizes were from about 200 mg to about 500 mg plaques. Each experiment includes five density measurements, so the density values are reported as the average and standard deviation of five measurements.

Preparation of Bisphenolic Coumarins and Coumarin-Based Polymers

Phloroglucinol, ethyl acetoacetate, ethyl propionyl acetate, ethyl 2-oxocyclohexane carboxylate, ethyl benzoylacetate, ethyl 4,4,4-trifluoroacetoacetate, zirconium tetrachloride, and (±)-epichlorohydrin were obtained from Millipore-Sigma (Burlington, Massachusetts) and used as received. Ethanol (EtOH), dichloromethane ($CH_2Cl_2$), and chloroform ($CHCl_3$) were obtained from Fisher Scientific (Hampton, New Hampshire) and used as received. 4,4'-methylenebis-2-ethyl-6 -methylaniline (MeEtMDA) was purchased from TCI Chemicals (Portland, Oregon) and used as received. Sodium hydroxide (NaOH) and magnesium sulfate ($MgSO_4$) were obtained from Polarchem Corp. (Garden Grove, California).

Synthesis of Substituted Bisphenolic Coumarins. Substituted bisphenolic coumarins were synthesized using phloroglucinol and a β-keto ester in a solvent-free Pechman reaction. The substituted bisphenolic coumarins, their acronyms, and the β-keto esters used to produce them are shown in Table 1. The substituted bisphenolic coumarins were isolated, recrystallized in EtOH, washed with chloroform, and then dried at 120° C. for 4 hours at 0.05 torr.

TABLE 1

| Substituted Bisphenolic Coumarin | | β-Keto Ester Used in |
|---|---|---|
| (Full Name) | (Acronym) | Pechman Reaction |
| 5,7-dihydroxy-4-methyl-2H-chromen-2-one | Me-CMRN | ethyl acetoacetate |
| 4-ethyl-5,7-dihydroxy-2H-chromen-2-one | Et-CMRN | ethyl propionyl acetate |
| 1,3-dihydroxy-7,8,9,10-tetrahydro-6H-benzo[c]chromen-6-one | C6-CMRN | oxocyclohexanecarboxylate |
| 5,7-dihydroxy-4-phenyl-2H-chromen-2-one | Ph-CMRN | ethyl benzoylacetate |

Synthesis of 4-methyl-5,7-bis(oxiran-2-ylmethoxy)-2H-chromen-2-one (Me-CMRN-EP). Me-CMRN-EP was synthesized a three-neck, 500 mL round-bottomed flask equipped with reflux condenser, addition funnel, and a magnetic stirring bar. 5,7-dihydroxy-4-methyl-2H-chromen-2-one (Me-CMRN; 14.00 g, 72.9 mmol), and (±)-epichlorohydrin (136 g, 115 mL, 1.47 mol) were added to the flask under a nitrogen atmosphere. The solution was heated to 90° C. followed by dropwise addition of a NaOH (5.97 g, 149 mmol) in EtOH (100 mL). The reaction was stirred for 4 hours at 90° C. then allowed to cool and filtered through a medium frit. The filtrate was concentrated under reduced pressure then the dissolved in dichloromethane (DCM) and washed with deionized (DI) water (3×250 mL) and brine (3×250 mL). The organics were then dried with $MgSO_4$, which was removed by filtration. The resulting organic layer was concentrated under reduced pressure (0.05 torr) at 100° C. for 16 hours to obtain the product as an orange solid (15.45 g, 69.7%, EEW=172.20; melting point (mp)=126° C. (DSC, $T_{peak\ endo}$=138° C.)). $^1H$ NMR (DMSO-$d^6$, 500 MHz) δ:6.63 (d, J=2.4 Hz, 1H, Ar), 6.57 (d, J=2.4 Hz, 1H, Ar), 6.05 (d, J=1.3 Hz, 1H, =CH), 4.49 (dd, J=11.4 Hz, 2.4 Hz, 2H, Ar—O—$CH_2$), 3.97-3.93 (m, 2H, Ar—O—$CH_2$), 3.47-3.44 (m, 1H, epoxide CH), 3.41-3.38 (m, 1H, epoxide CH), 2.91 (dt, J=7.4 Hz, 4.7 Hz, 2H, epoxide $CH_2$), 2.77-2.75 (m, 2H, epoxide $CH_2$), 2.56 (d, J=1.3 Hz, 3H, =C—$CH_3$). $^{13}C$ NMR ($CDCl_3$, 125 MHz) δ:24.5, 44.7, 50.3, 70.5, 71.4, 95.5, 97.8, 105.1, 112.0, 154.9, 157.1, 158.7, 160.5, 162.3. Anal. Calcd for $C_{18}H_{20}O_4$: C, 71.98; H, 6.71; O, 21.31. Found: C, 68.3; H, 5.95.

Synthesis of 4-ethyl-5,7-bis(oxiran-2-ylmethoxy)-2H-chromen-2-one (Et-CMRN-EP). In a similar manner as Me-CMRN-EP, Et-CMRN-EP was synthesized from 4-ethyl-5,7-dihydroxy-2H-chromen-2-one (Et-CMRN) and was obtained as a white solid (14.33 g, 78.8%, EEW=176.82; mp=104° C. (DSC, $T_{peak\ endo}$=109° C.)). $^1H$ NMR (DMSO-$d^6$, 500 MHz) δ:6.65 (d, J=2.4 Hz, 1H, Ar), 6.59 (d, J=2.4 Hz, 1H, Ar), 6.04 (s, 1H, —CH), 4.50 (td, J=11.4 Hz, 2.4 Hz, 2H, Ar—O—$CH_2$), 3.99-3.94 (m, 2H, Ar—O—$CH_2$), 3.46-3.43 (m, 1H, epoxide CH), 3.41-3.37 (m, 1H, epoxide CH), 2.97 (q, J=7.3 Hz, 3H, =C—$CH_2$), 2.91 (dt, J=11.8 Hz, 5.0 Hz, 2H, epoxide $CH_2$), 2.76 (dt, J=5.0 Hz, 2.7 Hz, 2H, epoxide $CH_2$), 1.22 (t, J=7.3 Hz, 3H, —$CH_3$). $^{13}C$ NMR ($CDCl_3$, 125 MHz) δ:14.8, 29.7, 44.6, 50.2, 70.5, 71.6, 95.7, 97.7, 104.4, 110.5, 157.4, 158.3, 160.2, 160.7, 162.2. Anal. Calcd for $C_{19}H_{23}O_4$: C, 72.59; H, 7.05; O, 20.36. Found: C, 64.14; H, 5.70.

Synthesis of 1,3-bis(oxiran-2-ylmethoxy)-7,8,9,10-tetrahydro-6H-benzo[c]chromen-6-one (C6-CMRN-EP). In a similar manner as Me-CMRN-EP, C6-CMRN-EP was synthesized from 1,3-dihydroxy-7,8,9,10-tetrahydro-6H-benzo[c]chromen-6-one (C6-CMRN). An additional drying step was required, and the organic layer was dried with 3 Å molecular sieves after drying with $MgSO_4$. The product was isolated as a yellow, glassy solid (17.17 g, 82.7%, EEW=190.02; $T_g$=25° C. (DSC)). $^1H$ NMR (DMSO-$d^6$, 500 MHz) δ:6.59 (d, J=2.4 Hz, 1H, Ar), 6.55 (d, J=2.4 Hz, 1H, Ar), 4.46 (dq, J=11.4 Hz, 2.5 Hz, 2H, Ar—O—$CH_2$), 3.92 (ddd, J=11.4 Hz, 6.7 Hz, 2.0 Hz, 2H, Ar—O—$CH_2$), 3.46-3.43 (m, 1H, epoxide CH), 3.40-3.37 (m, 1H, epoxide CH), 3.06 (bs, 2H, =C—$CH_2$), 2.91 (dt, J=8.0 Hz, 4.7 Hz, 2H, epoxide $CH_2$), 2.76 (dd, J=5.0 Hz, 2.7 Hz, 2H, epoxide $CH_2$), 2.41 (bs, J=5.0 Hz, 2.7 Hz, 2H, =C—$CH_2$), 1.69 (bs, 4H, —$CH_2$). $^{13}C$ NMR ($CDCl_3$, 125 MHz) δ:21.5, 22.7, 25.1, 30.1, 44.7, 50.3, 70.4, 71.4, 105.3, 119.4, 149.9, 155.0, 158.3, 161.0, 161.3. Anal. Calcd for $C_{21}H_{24}O_4$: C, 74.09; H, 7.11; O, 18.80. Found: C, 65.35; H, 5.85.

Synthesis of 5,7-bis(oxiran-2-ylmethoxy)-4-phenyl-2H-chromen-2-one (Ph-CMRN-EP). In a similar manner as Me-CMRN-EP, Ph-CMRN-EP was synthesized from 5,7-dihydroxy-4-phenyl-2H-chromen-2-one (Ph-CMRN) and was obtained as a pink solid (15.99 g, 79.27%, EEW=198.64; mp=116° C. (DSC, $T_{peak\ endo}$=131° C.)). $^1H$ NMR (DMSO-$d^6$, 500 MHz) δ:7.40 (dd, J=5.2 Hz, 1.8 Hz, 3H, Ar), 7.32 (m, 2H, Ar), 6.73 (d, J=2.4 Hz, 1H, Ar), 6.49 (d, J=2.4 Hz, 1H, Ar), 5.94 (s, 1H, =CH), 4.48 (dd, J=11.5 Hz, 2.5 Hz, 1H, Ar—O—$CH_2$), 3.97-3.91 (m, 2H, Ar—O—$CH_2$), 3.72-3.68 (m, 1H, epoxide CH), 3.38-3.35 (m, 1H, epoxide CH), 2.87 (t, J=4.9 Hz, 1H, epoxide $CH_2$), 2.73 (dd, J=5.0 Hz, 2.7 Hz, 1H, epoxide $CH_2$), 2.52 (q, J=4.7 Hz, 1H, epoxide $CH_2$), 2.43-2.40 (m, 1H, Ar—O—$CH_2$), 2.22 (dd, J=5.0 Hz, 2.7 Hz, 1H, epoxide $CH_2$). $^{13}C$ NMR ($CDCl_3$, 125 MHz) δ:44.3, 44.7, 49.5, 50.3, 70.7, 70.9, 95.8, 97.9, 103.8, 113.1, 128.0, 128.5, 128.8, 140.3, 156.0, 157.3, 157.8, 160.4, 162.9. Anal. Calcd for $C_{23}H_{22}O_4$: C, 76.22; H, 6.12; O, 17.66. Found: C, 68.85; H, 4.95.

Preparation of Polymeric Networks from Coumarin-Based Polymers

To generate polymeric networks, the epoxies synthesized from bisphenolic coumarins discussed above were mixed with an amine serving as a curing agent. Mixing ratios of the epoxy and amine were determined using the parts per hundred (phr) formula (3) from the epoxy equivalent weight (EEW) and amine hydrogen equivalent weight (AHEW) as follows:

$$phr = \frac{AHEW * 100}{EEW} \quad (3)$$

The epoxide equivalent weight (EEW) for the synthesized coumarin-based epoxies was determined via potentiometric titration in accordance with ASTM D1652. The AHEW value was calculated directly from the molecular weight of the amine and number of hydrogens.

The coumarin-based epoxy was added to a 4 mL vial with magnetic stirring bar and heated to 150° C. under nitrogen. After melting and degassing the epoxy, the amine was added to the vial, allowed to melt (typically in less than 1 minute), and mixed with the magnetic stirring bar on a hot plate until the mixture was homogenous. The epoxy-amine solution was then placed back in the oven at 150° C. until thermal equilibrium was re-established (e.g., for about 5 minutes). The total epoxy-amine solution weight was typically about 2.00 g.

The epoxy-amine solution was cast into aluminum molds to form six bars (about 20 mm×3 mm×2 mm) and two pucks (about 1.25 cm in diameter). The epoxy-amine mixtures were then cured under nitrogen with either cure protocol A (curing at 150° C. for 1 h, 180° C. for 2 hours, and 200° C. for 2 hours) or cure protocol B (curing at 180° C. for 8 hours). The network names and the epoxy-amine mixture compositions are shown in Table 2. Samples of Networks 1~4 were processed using cure protocols A, and additional samples were processed using cure protocol B. Samples of the 40:60 epoxy blend, Network 5, was processed using cure protocol B.

TABLE 2

| Network | Epoxy (wt %) | Curing Agent (wt %) |
|---|---|---|
| 1 | Me-CMRN-EP (71) | MeEtMDA (29) |
| 2 | Et-CMRN-EP (72) | MeEtMDA (28) |
| 3 | C6-CMRN-EP (73) | MeEtMDA (27) |
| 4 | Ph-CMRN-EP (74) | MeEtMDA (26) |
| 5 | Me-CMRN-EP (28.4); Et-CMRN-EP (43.2) | MeEtMDA (28.4) |

Evaluation of Bisphenolic Coumarins, Coumarin-Based Polymers and Polymer Networks The method produced the desired substituted bisphenolic coumarins, Me-CMRN, Et-CMRN, C6-CMRN, and Ph-CMRN, in yields of 63% to 74%. The coumarin-based epoxies obtained by epoxidizing the substituted bisphenolic coumarins with (±)-epichlorohydrin in yields of 70% to 83%.

The coumarin-based epoxies were analyzed via potentiometric titration to determine the epoxide equivalent weights (EEW). All the epoxy samples had were a blend of monomer and some oligomer. Me-CMRN-EP had an EEW of 172.20 g/mol epoxide, which is slightly higher than the theoretical value for the pure monomer ($EEW_{th}$=152.15 g/mol). Similar to Me-CMRN-EP, Et-CMRN-EP and C6-CMRN-EP had an EEW of 176.82 and 190.02, respectively, both being higher than the theoretical values for the pure monomer ($EEW_{th}$=159.17 and 172.18, respectively). Lastly, Ph-CMRN-EP had an EEW at 198.64, which was also higher than the theoretical value for the pure monomer ($EEW_{th}$=183.19) and the highest EEW of the coumarin-based epoxies synthesized. The EEW values for all coumarin-based epoxy samples highlights the formation of higher molecular weight oligomers (i.e. dimers, trimers, etc.).

Figure 2A:
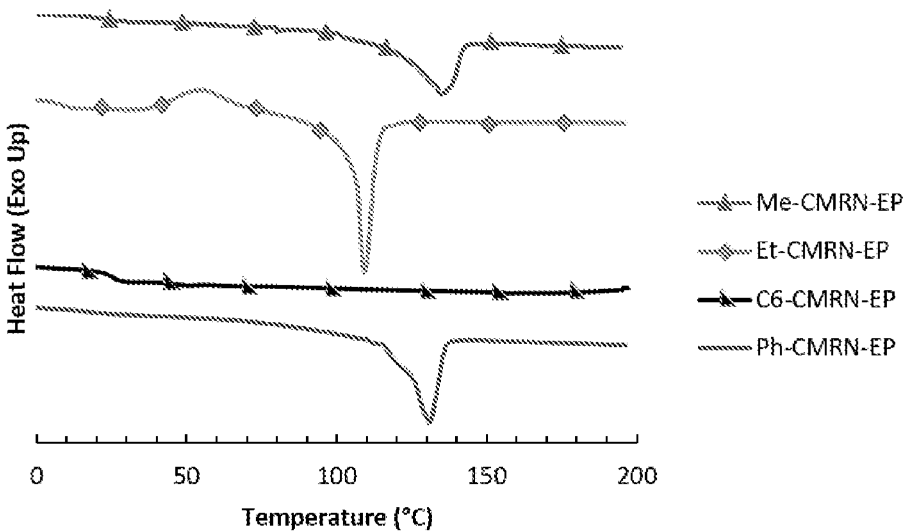
FIGS. 2(*a*) and 2(*b*) are graphs of differential scanning calorimetry (DSC) data of coumarin-based single component epoxies showing the melting behavior on the first heating cycle and second heating cycle, respectively.
Figure 2B:
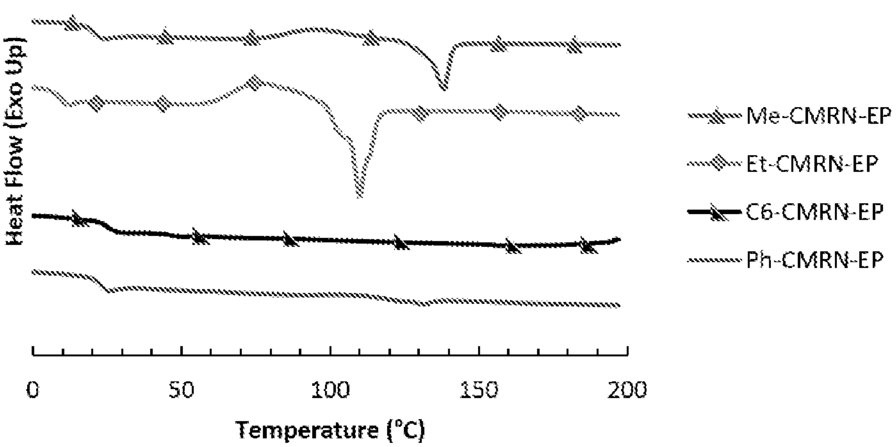

Thermal transitions of the coumarin-based epoxies were determined via DSC, and the results are shown in FIGS. 2(*a*) and 2(*b*). As shown in FIG. 2(*a*), Me-CMRN-EP and Ph-CMRN-EP had the highest melting points with melting onsets occurring at 126° C. and 116° C., respectively. Et-CMRN-EP had the lowest melting point at 104° C., whereas C6-CMRN-EP was an amorphous glassy solid and displayed a $T_g$ at 25° C. on both heating cycles. None of the coumarin-based epoxies showed crystallization during the cooling ramps of the DSC scans, but Me-CMRN-EP and Et-CMRN-EP both showed cold crystallization peaks on the second heating ramp prior to re-melting as shown in FIG. 2(*b*). To improve processability by lowering the melting point, a 40:60 blend of Me-CMRN-EP to Et-CMRN-EP by weight melted and mixed at 150° C. was analyzed by DSC. The resulting 40:60 coumarin-based epoxy blend had a $T_g$ of 13° C. on both heating cycles, and thus represents a significant improvement in processability with regard to that of the single component epoxies.

When preparing the coumarin-based polymer networks from mixtures of a coumarin-based epoxy and an amine as a curing agent, the resin systems for Networks 1 and 4 were mixed at high temperature prior to casting and curing because initial attempts to work with these resin systems between 100° C. and 140° C. resulted in recrystallization of the epoxy component. The resulting cured networks were heterogeneous with clear phase separation because multiple colors were observed throughout the samples (red domains and yellow domains). However, the Et-CMRN-EP and C6-CMRN-EP in the resin systems for Networks 2 and 3 did not readily recrystallize upon cooling and could be processed at lower temperatures, i.e. down to 100° C., after mixing and melting. The 40:60 Me-CMRN-EP to Et-CMRN-EP blend, prepared to further improve processability as discussed above, did not show a melting point. The resin system for Network 5, the epoxy blend cured with MeEtMDA at a ratio of 1:1 epoxide to amine hydrogen, could be mixed and cast at lower temperatures (e.g., at about 100° C.), which showed a significant improvement over the single epoxy networks.

Figure 3:
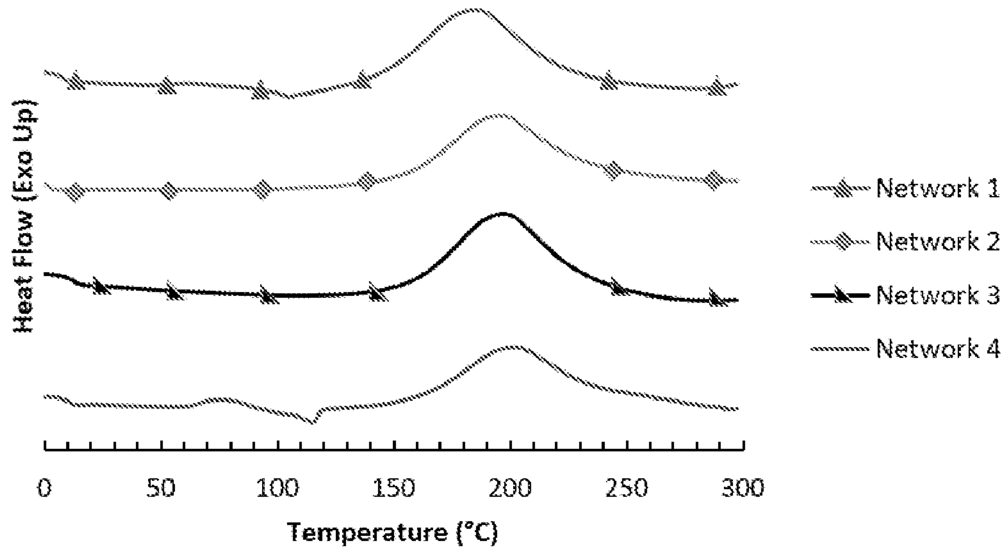
FIG. 3 is a graph of DSC data of coumarin-based epoxy networks, Networks 1-4, showing cold crystallization events and the curing reaction.

The cure chemistry of the coumarin-based epoxies was characterized using DSC via mixtures of a coumarin-based epoxy and an amine as shown in FIG. 3. The DSC data for Networks 1-4 is shown in Table 3. The peak exotherm temperatures presented in the table were determined using the Kissinger model.

TABLE 3

| Network | $T_{peak\ exo}$ (° C.)[1] | $\Delta H_{cure}$ (kJ/mol epoxide)[2] |
|---|---|---|
| 1 | 185 | 80 ± 13 |
| 2 | 195 | 95 ± 6 |
| 3 | 197 | 82 ± 13 |
| 4 | 202 | 89 ± 5 |

[1]Measured at a heating rate of 10° C./minute.

[2]Average enthalpy from scans with heating rates of 2, 4, 6, 8, and 10° C./minute.

As shown in FIG. 3, Network 1, composed of a mixture of Me-CRMN-EP at 71 wt. % and MeEtMDA, was most reactive with an onset of cure at about 125° C. and peak exotherm temperature of 185° C. However, a small, broad exotherm was observed between 50° C. to 90° C. and was followed by a small endotherm peaking at 107° C. Networks 2 and 3 had slightly higher peak exotherm temperatures with values of 195° C. and 197° C., respectively. The higher exotherm temperatures are likely due to the increased aliphatic content, which dilutes the epoxide functionality in Networks 2 and 3. No cold crystallization and melting events were observed for Networks 2 and 3. Network 4 had the highest peak exotherm temperature at 202° C. and showed a similar cold crystallization event with subsequent melting as Network 1.

The enthalpy of cure ($\Delta H_{cure}$) was determined for each network at different scanning rates (2, 4, 6, 8, and 10° C./minute) and averaged for comparison. The $\Delta H_{cure}$ values for Networks 1-4 were between 80 kJ/mol epoxide and 95 kJ/mol epoxide. The $\Delta H_{cure}$ values were likely due to cure during processing of the mixtures considering that the epoxy components typically had to be heated to 150° C. to fully melt, which is near or above the onset of cure for most networks. In addition, recrystallization of the epoxy component after mixing and cooling the epoxy-amine mixtures results in phase separation, which can also impact the $\Delta H_{cure}$ values due to the resulting heterogeneity of the mixtures.

Additional study of the cure kinetics of the coumarin-based polymer networks were studied using nonisothermal kinetic models and isothermal curing studies. The values for kinetic parameters activation energy ($E_a$) and collision factor (A) obtained for Networks 1-4 are summarized in Table 4. These values were estimated using the Kissinger method based on the peak exotherm temperature.

TABLE 4

| Network | $E_a$ (kJ/mol) | A | $R^2$ |
|---|---|---|---|
| 1 | 55 | 631 | 0.9997 |
| 2 | 56 | 563 | 0.9997 |
| 3 | 56 | 483 | 0.9998 |
| 4 | 57 | 550 | 0.9998 |

The $E_a$ values were consistent for all networks, ranging from 55 kJ/mol to 57 kJ/mol. However, significant differences in kinetic parameters were observed in the networks' collision factors. Network 1 had the highest collision factor of 631 likely due to the methyl-substituent being the smallest and less likely to sterically hinder the cure reaction or dilute the epoxide functionality. Network 2 and 4 had similar collision factors, 563 and 550, respectively. Network 3 had the lowest collision factor of 483 due to its bulky, fused cyclohexyl ring.

Figure 4:
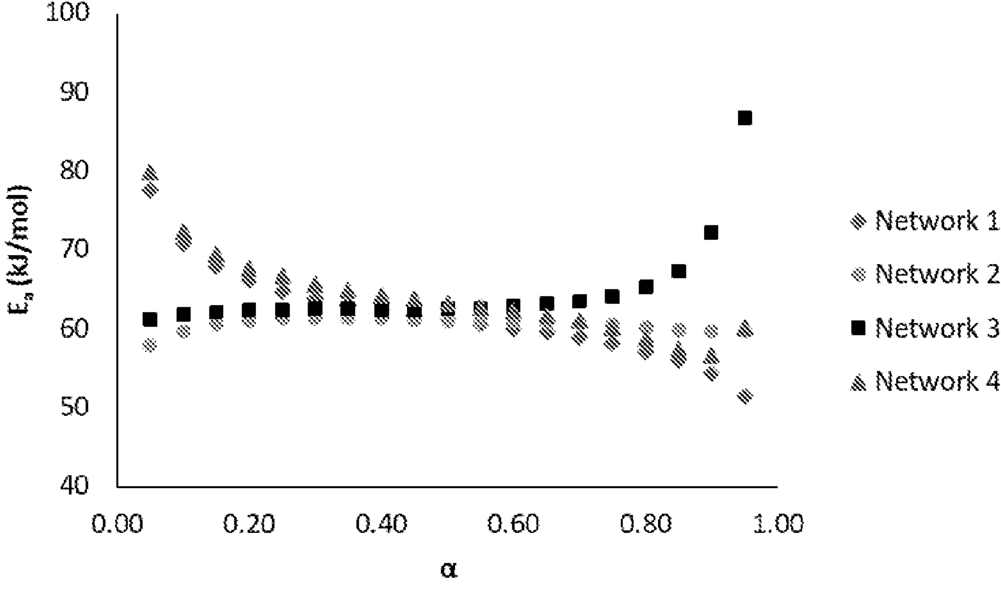
FIG. 4 is a graph of kinetic data for coumarin-based epoxy networks, Networks 1-4, derived using the Flynn-Wall-Ozawa model.

The cure kinetics were further studied to determine how the $E_a$ values change with conversion value, α, throughout the reaction using the Flynn-Wall-Ozawa model. The relationship between $E_a$ and α is shown for each network in FIG. 4. Networks 1 and 4 showed high initial $E_a$ values at α<0.25, but the values converge with the other networks at higher a values. Network 3 had low initial $E_a$ values, but the values increase sharply at α>0.70 suggesting a network with C6-CMRN-EP may be more difficult to fully cure than the other networks at high α values. However, at intermediate a values (0.3<α<0.7), the $E_a$ values for all four networks were consistent, which agrees with the values determined by the Kissinger model.

Figure 5:
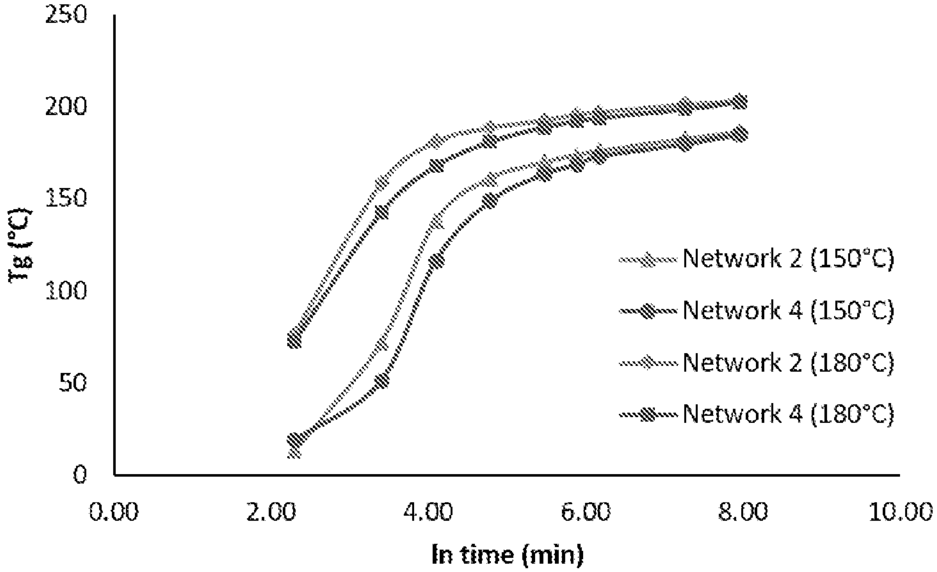
FIG. 5 is a graph of isothermal kinetic data for coumarin-based epoxy networks, Networks 1-4, showing relationship between $T_g$ and cure time.

To determine optimal curing protocols for the coumarin-based epoxy-amine networks, isothermal kinetics studies were performed on Networks 2 and 4. The results of these kinetic studies are shown in FIG. 5. Both networks had similar cure behavior at the selected isothermal temperatures (150° C. and 180° C.), which was expected based on the similar kinetic parameters observed in the Kissinger model. Vitrification was observed after 2 hours at each cure temperature and network. Also, Networks 2 and 4 had $T_g$ values of 203° C. after curing for 48 hours at 180° C.

To determine the $T_g$s of the cured networks, the networks were analyzed using dynamic-mode TMA. The results of the dynamic-mode TMA are summarized in Table 5. The networks cured with cure protocol A had much lower $T_g$s than the networks cured with cure protocol B. This difference in $T_g$s could be due to network phase separation at the low temperature step (i.e., at 150° C.) or decomposition at the high temperature step (i.e., at 200° C.). The networks had much higher $T_g$s when curing with cure protocol B likely because the temperatures were too high to favor phase separation over the curing reaction but not high enough to promote decomposition. All networks had $T_g$s>190° C. when using cure protocol B except Network 4, which had a $T_g$s of 187° C.

TABLE 5

| Network | Cure Protocol | Density (g/cm$^3$) | $T_g$, Storage (° C.) | $T_g$, Loss (° C.) | $T_g$, Tan δ (° C.) |
|---|---|---|---|---|---|
| 1 | A | 1.2419 ± 0.0002 | 151.3 ± 11.1 | 167.8 ± 11.2 | 174.1 ± 10.1 |
| 2 | A | 1.2385 ± 0.0002 | 160.2 ± 6.5 | 167.2 ± 3.0 | 181.8 ± 18.7 |
| 3 | A | 1.2500 ± 0.0001 | 127.1 ± 6.2 | 147.9 ± 9.5 | 155.0 ± 10.4 |
| 4 | A | 1.2299 ± 0.0002 | 134.2 ± 10.3 | 145.1 ± 15.1 | 150.4 ± 14.3 |
| 1 | B | 1.2659 ± 0.0019 | 190.0 ± 15.7 | 204.1 ± 5.2 | 210.9 ± 1.4 |
| 2 | B | 1.2570 ± 0.0050 | 199.7 ± 2.0 | 202.1 ± 0.4 | 206.1 ± 0.6 |
| 3 | B | 1.2559 ± 0.0008 | 194.6 ± 8.4 | 202.3 ± 7.7 | 212.7 ± 1.3 |

TABLE 5-continued

| Network | Cure Protocol | Density ($g/cm^3$) | $T_g$, Storage (° C.) | $T_g$, Loss (° C.) | $T_g$, Tan δ (° C.) |
|---|---|---|---|---|---|
| 4 | B | 1.2556 ± 0.0005 | 187.1 ± 1.3 | 191.9 ± 1.1 | 197.3 ± 1.7 |
| 5 | B | 1.2531 ± 0.0022 | 196.9 ± 14.6 | 207.2 ± 1.2 | 212.1 ± 1.2 |

Figure 6A:
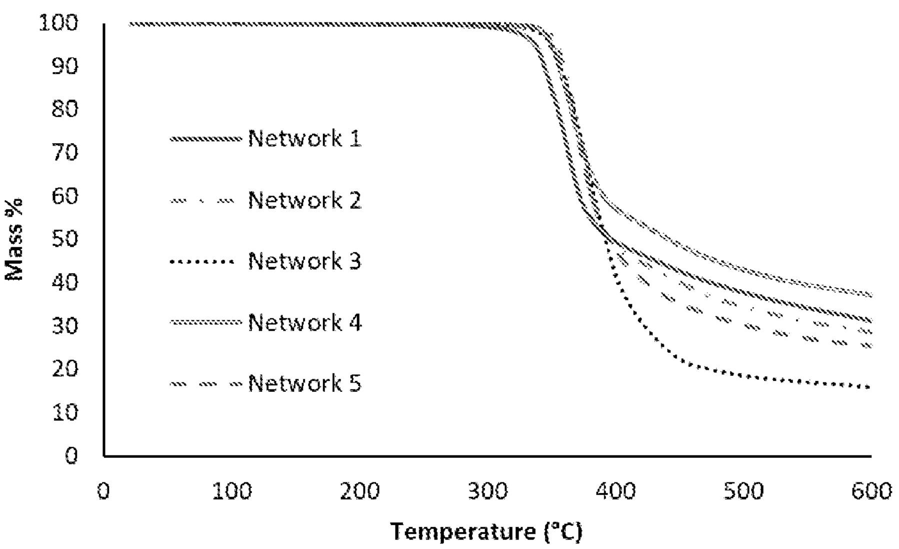
FIGS. 6(*a*) and 6(*b*) are graphs showing thermogravimetric analysis (TGA) results for coumarin-based epoxy networks, Networks 1-5, in nitrogen and in air, respectively.
Figure 6B:
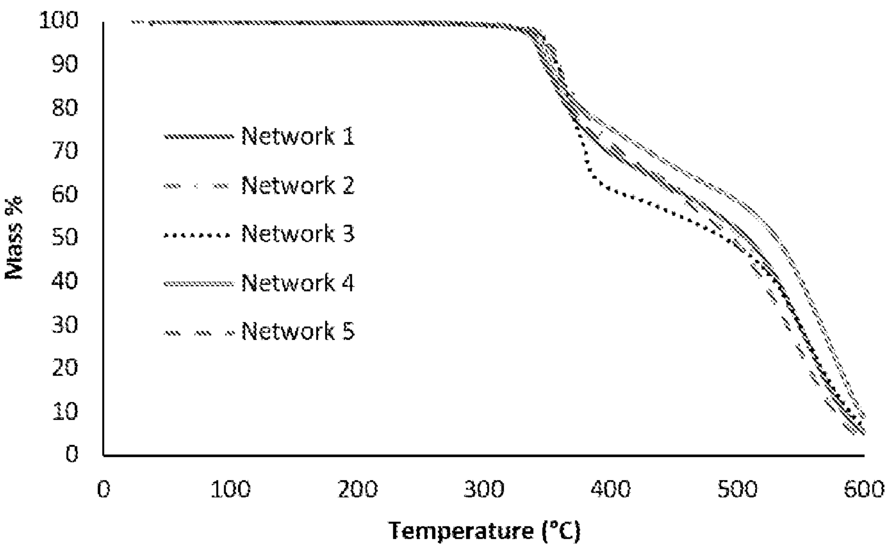

The decomposition behavior of the cured networks was examined in nitrogen and air, and the results are summarized in Table 6. FIGS. 6(*a*) and 6(*b*) show the TGA thermograms in nitrogen and in air, respectively, for the networks cured with cure protocol B. The results were fairly consistent for all networks with decomposition temperatures around 350° C. in both nitrogen and air regardless of cure protocol with the exception of Network 1, which had a decomposition temperature of 324° C. in both atmospheres.

TABLE 6

| Network | Cure Protocol | $T_{d5\%}$, $N_2$ (° C.) | Char Yield, $N_2$ (wt %) | $T_{d5\%}$, Air (° C.) | Char Yield, Air (wt %) |
|---|---|---|---|---|---|
| 1 | A | 324 ± 2 | 27 ± 1 | 325 ± 2 | 5 ± 1 |
| 2 | A | 354 ± 1 | 24 ± 1 | 355 ± 1 | 4 ± 1 |
| 3 | A | 354 ± 5 | 12 ± 1 | 352 ± 3 | 5 ± 1 |
| 4 | A | 349 ± 2 | 30 ± 1 | 351 ± 4 | 6 ± 2 |
| 1 | B | 339 ± 3 | 33 ± 1 | 343 ± 3 | 5 ± 1 |
| 2 | B | 354 ± 1 | 29 ± 1 | 354 ± 1 | 5 ± 1 |
| 3 | B | 349 ± 1 | 16 ± 1 | 350 ± 1 | 6 ± 1 |
| 4 | B | 351 ± 1 | 37 ± 1 | 347 ± 1 | 8 ± 2 |
| 5 | B | 351 ± 2 | 24 ± 1 | 352 ± 1 | 4 ± 1 |

As shown in Table 6, the char yields of the coumarin epoxy networks ranged from 12-37% in nitrogen depending on cure protocol and epoxy substituents. The char yield dropped with increasing aliphatic substitution with Network 1 having the highest char yields (27% with cure protocol A and 33% with cure protocol B), Network 3 having the lowest char yields (12% with cure protocol A and 16% with cure protocol B), and Network 2 having intermediate values (24% with cure protocol A and 29% with protocol B). Similar to Network 2, Network 5 had intermediate values (24% with protocol B). The char yields of Network 4 improved to 30% and 37% with cure protocol A and B, respectively, due to the higher aromatic content of Ph-CMRN-EP. The char yields in air were less than 8% for all of the networks.

What is claimed is:

1. A method for synthesizing a sustainable bisphenolic coumarin, the method comprising:

(a) providing a phloroglucinol and at least one β-keto ester, where the phloroglucinol is derived from biological source materials;

(b) placing the phloroglucinol, the at least one β-keto ester, and a catalyst in a reaction vessel;

(c) heating the reaction vessel; and (d) allowing the phloroglucinol to react with the at least one β-keto ester for a reaction time in the range of about 5 minutes to about 30 minutes, thereby producing bisphenols having a coumarin-based structure.

2. The method of claim 1, wherein the phloroglucinol is produced by fermenting biological materials or generated from naringenin.

3. The method of claim 1, wherein the at least one β-keto ester is selected from ethyl acetoacetate, ethyl-2-oxocyclohexane carboxylate, ethyl benzoylacetate, ethyl-4,4,4-trifluoroacetoacetate, or a combination thereof.

4. The method of claim 1, wherein heating the reaction vessel comprises heating the reaction vessel to a temperature in the range from about 50° C. to about 150° C.

5. The method of claim 1, wherein the catalyst is an acid catalyst.

6. The method of claim 5, wherein the acid catalyst comprises a Lewis acid catalyst.

7. The method of claim 1, the method further comprising purifying the bisphenolic coumarin by recrystallizing the bisphenolic courmarin and washing the recrystallized bisphenolic coumarin with a non-polar solvent.

8. A method for making a coumarin-based polymeric material, the method comprising:

providing a purified bisphenolic coumarin synthesized using the method of claim 7; and converting the purified bisphenolic coumarin into a thermoplastic or a thermosetting resin.

9. The method of claim 8, wherein the thermoplastic comprises polycarbonates, polyesters, and polysulfones.

10. The method of claim 8, wherein the thermosetting resin comprises epoxies, cyanate esters, propargyl ethers, and phthalonitriles.

11. The method of claim 8, where converting the purified bispohenolic coumarin into a thermosetting resin comprises epoxdizing the purified bisphenolic coumarin via substitution reaction with a (±)-epichlorohydrin, thereby producing a coumarin-based epoxy.

* * * * *